(12) United States Patent  (10) Patent No.: US 7,945,016 B2
Bothorel et al.  (45) Date of Patent: May 17, 2011

(54) DENTAL RADIOLOGY APPARATUS AND ASSOCIATED METHOD OF USE

(75) Inventors: Sylvie Bothorel, Paris (FR); Vincent Loustauneau, Fontenay-Sous-Bois (FR); Jean-Marc Inglese, Bussy-Saint-Georges (FR)

(73) Assignee: Trophy, Croissy Beaubourg (FR)

( * ) Notice: Subject to any disclaimer, the term of this patent is extended or adjusted under 35 U.S.C. 154(b) by 144 days.

(21) Appl. No.: 12/546,201

(22) Filed: Aug. 24, 2009

(65) Prior Publication Data

US 2010/0074402 A1 Mar. 25, 2010

(30) Foreign Application Priority Data

Aug. 22, 2008 (FR) ..................................... 08 55681

(51) Int. Cl.
*A61B 6/14* (2006.01)
*H05G 1/60* (2006.01)
*H05G 1/64* (2006.01)
*G21K 1/02* (2006.01)

(52) U.S. Cl. ............ 378/38; 378/19; 378/148; 378/191; 378/196; 378/197

(58) Field of Classification Search .................... 378/19, 378/20, 38, 148, 149, 191, 196, 197
See application file for complete search history.

(56) References Cited

U.S. PATENT DOCUMENTS

| | | | |
|---|---|---|---|
| 5,677,940 A * | 10/1997 | Suzuki et al. .................... | 378/38 |
| 6,289,074 B1 | 9/2001 | Arai et al. | |
| 6,493,415 B1 * | 12/2002 | Arai et al. ......................... | 378/4 |
| 7,322,746 B2 * | 1/2008 | Beckhaus et al. ............. | 378/205 |
| 7,347,622 B2 * | 3/2008 | Sadakane et al. ............. | 378/197 |
| 7,486,759 B2 * | 2/2009 | Suzuki et al. .................... | 378/4 |
| 7,577,232 B2 * | 8/2009 | Tachibana et al. .............. | 378/39 |
| 7,711,085 B2 * | 5/2010 | Suzuki et al. ................... | 378/39 |
| 7,720,191 B2 * | 5/2010 | Muller ............................. | 378/38 |
| 7,773,720 B2 * | 8/2010 | Honjo et al. ..................... | 378/19 |
| 7,787,586 B2 * | 8/2010 | Yoshimura et al. .............. | 378/4 |
| 7,798,708 B2 * | 9/2010 | Erhardt et al. ................ | 378/191 |
| 2009/0052616 A1 | 2/2009 | Honjo et al. | |
| 2010/0172462 A1 * | 7/2010 | Tancredi et al. .................. | 378/4 |

FOREIGN PATENT DOCUMENTS

| | | |
|---|---|---|
| EP | 1491145 | 12/2004 |
| WO | 2006109802 | 10/2006 |

OTHER PUBLICATIONS

French search report dated, Mar. 12, 2009, from corresponding French application.

\* cited by examiner

*Primary Examiner* — Allen C. Ho
(74) *Attorney, Agent, or Firm* — Young & Thompson

(57) ABSTRACT

A dental radiology apparatus includes:
a generator (18) emitting X-radiation provided with a collimation device collimating the radiation in an appropriate manner using several forms of collimation slits,
at least one radiation sensor (20a, 20b) including a first, a second and a third image acquisition surface which are each positioned opposite an appropriate form of slit in order to use the apparatus in panoramic mode, cone beam tomographic mode and mode determining a trajectory which will be used in panoramic mode respectively. In the third mode a form of slit elongated along a plane P is arranged opposite the third surface corresponding to a part of the second surface along a Z-axis perpendicular to the plane P and the assembly is driven in rotation about an axis parallel to the Z-axis.

37 Claims, 9 Drawing Sheets

DENTAL RADIOLOGY APPARATUS AND ASSOCIATED METHOD OF USE

The present invention relates to a dental radiology apparatus and a method for using this apparatus.

In the field of dental radiology, radiology apparatuses are known which comprise an X-ray generator and an X-ray sensor each mounted on an arm with an arch-shaped structure, for example within the framework of acquisitions of panoramic or cone beam tomographic images.

There are apparatuses which allow only panoramic photographs to be taken and others which are capable of producing both panoramic images and cone beam tomographic images.

The second type of apparatus comprises two types of sensors and an X-ray generator equipped with two collimation slits. For each of the two types of operation, namely the panoramic mode and the cone beam tomographic mode, one of the two sensors associated with one of the two slits is used.

More particularly, for the operation of the apparatus in panoramic mode, the X-ray generator is provided with a vertical collimation slit (first slit) and one of the sensors (first sensor) is made in the form of an array of pixels placed behind a vertical slit arranged opposite the first slit of the generator.

The object to be radiographed is placed between the X-ray generator and the first sensor. The X-rays are emitted by the generator in the form of a cone collimated by the slit in the direction of the object. The sensor receives the rays that have illuminated the object, converts them into electrical signals and provides at the output an image signal of the illuminated object.

When it is desired to produce, with this type of apparatus, a radiograph of a patient's jaw and in particular to obtain a panoramic image of it, the patient is placed in a sitting or standing position under the arch, between the generator and the sensor.

The arch pivots about a vertical axis of rotation while the jaw is illuminated by the X-rays in order that the sensor can provide image signals of the patient's jaw.

Simultaneously with the rotation movement, the axis of rotation of the arch describes a trajectory in the shape of a horseshoe which follows the shape of the patient's dental arch. The zone of interest under investigation (dental arch) covers the jaw.

However, as the generator and the sensor are placed on either side of the patient, during the rotation bony structures will be superposed on the jaw in the resultant image captured by the sensor.

In order to limit the effects of this superposition, the pixels of the sensor are shifted at a rate which is governed by the movement and position of the arch. This gives rise to a kinetic blurring such that the undesirable bony structures mentioned above manifest themselves in horizontal bands (streaking) which limit the inconvenience when establishing a diagnosis.

Moreover, the procedure is such that the pixels of the sensor which are read shifted in the opposite direction to the movement of travel along the trajectory remain fixed in relation to the plane of the arch located in the focal trough.

This technique, which also contributes to a better dosimetric balance, is known under the name of TDI ("Time Delay Integration").

The combination of the rotational speed of the arch, the trajectory of the centre of rotation and the translation speed of the pixels on the sensor allows a focal trough to be obtained which has the shape of a band of greater or lesser width which follows the patient's dental arch. The objects located on either side of this focal trough manifest themselves in streaking.

In the resultant image which presents itself as a developed image of the patient's jaw, the objects located in the focal trough will stand out clearly from the streaking caused by the objects located on either side of this zone, thus facilitating diagnosis.

The displacement of the sensor and the generator along this trajectory is achieved using a servo-motor mechanism (for example an X,Y-controlled table) placed above the arch and controlled to steer the movement along the X- and Y-axes in the plane of rotation of the sensor and the generator.

The control of this mechanism requires knowledge of the trajectory matched to the shape of the patient's dental arch.

When producing panoramic pictures, the operator of the apparatus does not have available information allowing him to control the displacement of the sensor and the generator in a manner matched to the patient's jaw.

Thus, the apparatus very often makes several standard forms of dental arch available to the operator from which he selects the one that seems to him to be the most suitable for the patient to be radiographed. These standard forms are based on statistical data of typical morphologies. The apparatus is then programmed in order that the assembly formed of the sensor and the generator travels the trajectory corresponding to the selected standard form of arch (the trajectory is defined as being the median line between the two opposite edges of the standard form of the dental arch).

However, this solution is not entirely satisfactory, since the sensor and the generator are not positioned in a manner matched to the morphology of the patient's jaw.

Problems of clarity may result for the zone of interest in the image obtained in this way. For example, the patient's teeth cannot be completely registered in the standard form of arch selected by the operator.

Moreover, the selection process which has just been described requires the operator to carry out several manoeuvres in order to obtain a panoramic image which, moreover, is sometimes vague over certain zones of the dental arch (incisors, molars . . . ).

In the light of the above, it would be useful to have available an apparatus and an associated method which allow at least a partial contribution to the resolution of at least one of the problems described above.

The present invention thus proposes a dental radiology apparatus comprising:
- a generator provided with a window emitting X-radiation and a collimation device positioned in front of said window in order to collimate the radiation in a suitable manner using several forms of collimation slits,
- at least one sensor comprising a first image acquisition surface elongated along a Z-axis perpendicular to a plane P and being used in a first position of the apparatus to produce a panoramic image of a jaw placed between the generator and the first image acquisition surface, the panoramic image being produced from the X-radiation collimated by a first form of collimation slit elongated along the Z-axis and received by the first sensor image acquisition surface and by displacement of the generator and of said first surface along a given trajectory in the plane P combined with a rotation about an axis parallel to the Z-axis, the said at least one sensor comprising a second image acquisition surface used in cone beam tomographic mode, in a second position of the apparatus, to produce a three-dimensional model of only a part of the jaw from the X-radiation collimated by a second form of collimation slit and received by the second image acquisition surface and by displacement of the generator and said second surface in rotation about an axis parallel to the Z-axis, the second form of collimation slit having dimensions matched to those of the second image acquisition surface, characterized in that the apparatus is able to occupy a third position of use and to this end comprises means of positioning, in front of the window emitting X-radiation, a third form of collimation slit elongated in a direction parallel to the plane P and arranged opposite a third image acquisition surface corresponding to a part of the second surface along the Z-axis in order to cooperate with the third image acquisition surface, the longitudinal dimension of the slit in the direction parallel to the plane P being matched to the dimension of the second image acquisition surface in this same direction.

The apparatus which is capable of operating in panoramic mode and in cone beam tomographic mode is thus given a new mode of operation using cone beam tomography as an intermediate mode (third position of the apparatus) with a view to determining a trajectory to be travelled by the said at least one sensor and the first slit during the subsequent production of panoramic images.

In this intermediate mode, the apparatus is configured by the arrangement of a third form of collimation slit elongated in the plane P opposite the first image acquisition surface which is used normally in cone beam tomography.

More particularly, this new configuration of dental radiology apparatus gives the apparatus a new functionality that allows a three-dimensional model of a part of the jaw to be obtained (by cone beam tomography). The adapted dimensions of the form of third slit oriented in this way and of the first image acquisition surface allow a three-dimensional model of only part of the width of the jaw to be obtained. This three-dimensional model contains data which will be used by the apparatus when it operates in conventional panoramic mode to produce a panoramic image.

It will be noted that this new arrangement of the apparatus is used to produce several three-dimensional models of different parts of the object.

Thus, according to a feature, the apparatus comprises means of obtaining in cone beam tomographic mode a predetermined number of three-dimensional models each representing a different part of a jaw from an assembly comprising second image acquisition surface and generator provided with the third form of collimation slit elongated parallel to the plane P.

This plurality of three-dimensional models provides the necessary data allowing the panoramic mode of operation of the apparatus to be improved.

To do this, the number of three-dimensional models is chosen so as to cover the part of a jaw located above and below the occlusal zone (part of the two dental arches where the teeth touch).

More particularly, the apparatus comprises:
means of positioning, in the plane P, about a fixed axis parallel to the Z-axis, the assembly comprising third image acquisition surface and generator provided with the third form of collimation slit elongated parallel to the plane P;
means of driving in rotation, about the fixed axis of rotation, the assembly comprising third surface and generator;
means of acquiring several image signals of a part of a jaw illuminated by the radiation collimated by the third form of slit oriented parallel to the plane P for a plurality of angular positions occupied by the third assembly comprising surface and generator during the rotation movement.

These means which are specific to an apparatus operating in tomographic mode allow, in combination with the form of slit oriented parallel to the plane P and the longitudinal dimension of which is suitable for the width of the second image acquisition surface, image signals of a part of a jaw to be acquired.

The height of this part of the jaw does not correspond to the total height of the jaw, but this is not important taking account of the fact that the sought information is located substantially in the occlusal zone.

According to a feature, the positioning means are able to position the assembly comprising third image acquisition surface and generator provided with the third form of collimation slit elongated parallel to the plane P successively about other fixed axes of rotation in order that, for each positioning about one of these other axes of rotation, the drive means and the acquisition means are able to cooperate with a view to acquiring image signals of another illuminated part of the jaw.

Thus, by displacing the axis of rotation in a suitable manner relative to selected zones of the jaw, it is possible to obtain image signals of the zone concerned.

According to a feature, the apparatus comprises means of obtaining a three-dimensional model of each illuminated part of a jaw from the set of acquired image signals.

Thus, a three-dimensional model of an illuminated part of a jaw can be obtained after each acquisition of the set of image signals of the part concerned or once the sets of image signals have been acquired for all the parts of the jaw.

This latter method provides for the grouping of the acquisition of all the image signals during a single phase in order to immobilize the patient for as short a time as possible.

This allows the risk of errors if the patient moves to be reduced.

According to a feature, the apparatus comprises:
means of reconstructing a three-dimensional model of a jaw from the three-dimensional models of the different parts of a jaw; and
means of identifying, from the three-dimensional model reconstructed in this way, a trajectory which the assembly comprising first image acquisition surface and generator will have to follow during the subsequent production of a panoramic image of the jaw.

When the three-dimensional models of the selected different zones or parts of the jaw have been obtained, they are then grouped within a three-dimensional model which represents the whole of the jaw over its whole width (over a reduced height relative to the total height of the jaw).

The apparatus comprises means allowing the obtaining, by cone beam tomography, from the three-dimensional model reconstructed in this way, of a trajectory suitable for the object to be radiographed. During the subsequent development of a panoramic image of this object, the displacement of the apparatus will be guided along this trajectory in order that the first image acquisition surface and the generator follow the contours of the object as closely as possible, i.e. as faithfully as possible.

The result is that the panoramic image of the object that will be generated will be of better quality than previously. In fact, it is thus ensured that the object (dental arches) is in the focal trough.

Moreover, the operator will not need to choose from standard types of dental arches, which will limit the risk of errors and manoeuvres.

According to a feature, the means of identifying a trajectory from the reconstructed three-dimensional model comprise means of thresholding or segmenting the data constituting this three-dimensional model.

According to a feature, the collimation device comprises three collimation slits of different forms which are each able to be positioned, on command, in front of the emission window in order to collimate the radiation in an appropriate manner.

The apparatus is thus equipped with three collimation slits, each of them being dedicated to a particular mode of operation (position of use of the apparatus).

According to a feature, the collimation device comprises a mobile collimation slits support which is able to position, under the action of positioning means, a collimation slit in front of the window emitting X-radiation.

This device thus allows the slits to be switched in a suitable manner according to the mode of operation programmed for the apparatus.

According to a feature, the collimation slits support is able to pivot under the action of the positioning means.

According to a feature, the collimation device comprises a collimation slit and means of adjusting the dimensions of the slit in order to give it at least some of the three forms of collimation slit used in the three respective positions of the apparatus.

The apparatus is thus equipped with a variable-geometry slit.

According to another feature, the adjustment means are means of adjusting the elongation of the slit in directions perpendicular to each other.

According to a feature, the adjustment means are independent as regards the directions.

According to a feature, the collimation slit is delimited by four edges and the adjustment means are able to displace each of the edges independently of one another.

According to a feature, each first, second and third image acquisition surface of the said at least one sensor is an array of pixels or a sub array of pixels.

According to a feature, the predetermined number of three-dimensional models depends in particular on the size of the array of pixels or of the sub array of pixels of the third image acquisition surface.

In fact, the size of the array or of the sub array limits the volume of the part of the jaw that is scanned using cone beam tomography and thus dictates the number of "elementary volumes" necessary to obtain a three-dimensional model of the jaw over its whole width, above and below the occlusal zone but not over its whole height.

According to a feature, the means of acquiring several image signals comprise means of reading the data captured by the array or the sub array of pixels, said reading means comprising means of grouping the pixels according to a predetermined number of pixels for the purpose of reading the pixels grouped in this way.

The grouping of pixels allows a reduction of the dose of X-rays used to operate the apparatus with the second image acquisition surface in intermediate mode (trajectory-determination mode).

Although spatial resolution is lost in the image acquired during the grouping of pixels, this is not harmful taking account of the sought information.

According to a feature, the first and second image acquisition surfaces form part of a first and a second sensor respectively.

These two sensors are different physically. One of the sensors is suitable solely for the panoramic mode (acquisition of panoramic images by linear tomography), while the other is suitable for the cone beam tomographic mode in order to acquire a solid image of a "small field" (typically, this corresponds to an image of a dental half-arch).

This arrangement thus allows one or other of the sensors to be positioned easily and in a controlled manner (for example using a control system involving a computer/computer-controlled system) according to the selected mode of operation.

According to a feature, the first, second and third image acquisition surfaces form part of a single sensor.

A single sensor is thus available, one or more image acquisition surfaces of which are used which correspond to the totality of the sensitive surface (active detection surface) of the sensor or to a part of this according to the desired mode of operation.

The selection of a given image acquisition surface can be made simply by reading/not reading the pixels located in the surface/outside the surface.

With a sensor of large dimensions which allows a complete skull to be captured in cone beam tomographic mode, only a reduced surface of this sensor (third image acquisition surface) is used in the intermediate mode of operation (determination of trajectory), not reading the pixels of the second surface arranged outside the third surface. This allows the doses of radiation used to be reduced.

Another object of the invention is a method for producing a panoramic image of a patient's jaw from a dental radiology apparatus comprising:

a generator provided with a window emitting X-radiation and a collimation device positioned in front of said window in order to collimate the radiation in a suitable manner using several forms of collimation slits, at least one sensor comprising a first image acquisition surface elongated along a Z-axis perpendicular to a plane P and being used in a first position of the apparatus to produce a panoramic image of a jaw placed between the generator and the first image acquisition surface, the panoramic image being produced from the X-radiation collimated by a first form of collimation slit elongated along the Z-axis and received by the first sensor image acquisition surface and by displacement of the generator and of said first surface along a given trajectory in the plane P combined with a rotation about an axis parallel to the Z-axis, the said at least one sensor comprising a second image acquisition surface used in cone beam tomographic mode, in a second position of the apparatus, to produce a three-dimensional model of only a part of the jaw from the X-radiation collimated by a second form of collimation slit and received by the second image acquisition surface and by displacement of the generator and of said second surface in rotation about an axis parallel to the Z-axis, the second form of collimation slit having dimensions matched to those of the second image acquisition surface, characterized in that the method comprises, in a third position of use of the apparatus in cone beam tomographic mode, the following preliminary steps in order to obtain a trajectory which will be travelled in the plane P, by the assembly comprising generator and first image acquisition surface, in the first position of use of the apparatus for the production of a panoramic image of the jaw:

positioning, in front of the window emitting X-radiation, of a third form of collimation slit elongated in a direction parallel to the plane P and the longitudinal dimension of which in this direction is matched to the dimension of the second image acquisition surface in this same direction, positioning, opposite the third form of collimation slit oriented in this way, of a third image acquisition surface corresponding to a part of the second surface along the Z-axis, for the purpose of cooperation of the third form of slit and the third surface.

This method thus provides for a temporary switch to an intermediate mode of tomographic operation (trajectory-determination mode) in order to acquire data which will be used to improve the operation of the apparatus in panoramic mode and, in particular, to enhance the quality of the panoramic images.

This switch is carried out by changing the configuration/position of the apparatus.

In particular, a new orientation/form of slit is combined with the second image acquisition surface instead of the second form of slit which is normally used for cone beam tomography.

According to a feature, the method comprises, following the positioning steps, a step of obtaining in cone beam tomographic mode a predetermined number of solid images each representing a different part of a jaw from the assembly comprising second image acquisition surface and generator provided with the third form of collimation slit elongated parallel to the plane P.

According to a feature, the method comprises the following steps:

a) positioning in the plane P, about a fixed axis parallel to the Z-axis, of the assembly comprising second image acquisition surface and generator provided with the third form of collimation slit elongated parallel to the plane P;

b) driving in rotation of the assembly comprising second image acquisition surface and generator about the fixed axis of rotation;

c) acquisition of several image signals of a part of a jaw illuminated by the radiation collimated by the third form of slit oriented parallel to the plane P for a plurality of angular positions occupied by the assembly comprising second image acquisition surface and generator during the rotation movement.

According to a characteristic feature, the method also comprises the following steps:

positioning of the assembly comprising second image acquisition surface and generator provided with the third form of collimation slit elongated parallel to the plane P about another fixed axis parallel to the Z-axis and realization of steps b) and c) for the acquisition of the image signals of another illuminated part of the jaw.

It will be noted that the aforementioned combination of the two steps is carried out for the number of times which is necessary to acquire image signals over the whole width of the jaw.

According to a feature, the method comprises a step of obtaining, from the set of acquired image signals, a three-dimensional model of each illuminated part of the jaw.

According to a feature, the method comprises the following steps:

reconstruction of a three-dimensional model of a jaw from the three-dimensional models of different parts of a jaw;

identification, from the three-dimensional model reconstructed in this way, of a trajectory which the assembly comprising first image acquisition surface and generator will have to follow during the subsequent production of a panoramic image of the jaw.

According to a feature, the identification of a trajectory from the reconstructed three-dimensional model comprises a step of thresholding or segmenting the data constituting this three-dimensional model.

According to a feature, the method comprises the following steps:

positioning, in front of the window emitting X-radiation, of the first form of collimation slit elongated along the Z-axis, positioning of the first image acquisition surface opposite the first form of collimation slit oriented in this way, control of the displacement of the assembly formed of the generator provided with the first form of collimation slit and the first image acquisition surface arranged parallel to the Z-axis along the previously obtained trajectory combined with a rotation movement about an axis parallel to the Z-axis, acquisition of a panoramic image of the jaw during this controlled displacement combined with a shift of the pixels of the first image acquisition surface.

Thus, once the trajectory is determined with the intermediate tomographic mode of operation, the method provides for the switch to the panoramic mode of operation.

To do this, the configuration/position of the apparatus is once again modified. The third form of slit and the second image acquisition surface are replaced by the first form of slit and the first image acquisition surface respectively which are normally combined in panoramic mode.

The obtained trajectory thus allows the precise and reliable programming of the displacement of the first sensor image acquisition surface and the generator provided with the first form of slit in the plane in order to produce a final image of high quality.

According to a feature, the collimation device comprises three collimation slits of different forms and the positioning of each of them in front of the emission window is carried out by displacement from a home position placed outside the radiation that has come from the generator.

According to a feature, the collimation device comprises a collimation slit and the positioning, in front of the emission window, of a different form of collimation slit is carried out by adjusting the dimensions of the slit.

According to a feature, the adjustment more particularly comprises the adjustment of the elongation of the slit in directions perpendicular to each other.

According to a feature, each first, second and third image acquisition surface of the said at least one sensor is an array of pixels or a sub array of pixels.

According to a feature, the predetermined number of three-dimensional models depends in particular on the size of the array or the sub array of pixels of the third image acquisition surface.

According to a feature, the acquisition of several image signals comprises a step of reading the data captured by the array or the sub array of pixels which comprises a grouping of the pixels according to a predetermined number of pixels for the purpose of reading the pixels grouped in this way.

According to a feature, the first and second image acquisition surfaces form part of a first and a second sensor respectively.

According to a feature, the positioning of a sensor opposite the generator is carried out by displacement of said sensor.

According to a feature, the first, second and third image acquisition surfaces form part of a single sensor.

Other details and advantages of the invention will appear during the description given below in non-limitative manner with reference to the attached drawings, in which.

Figure 1:
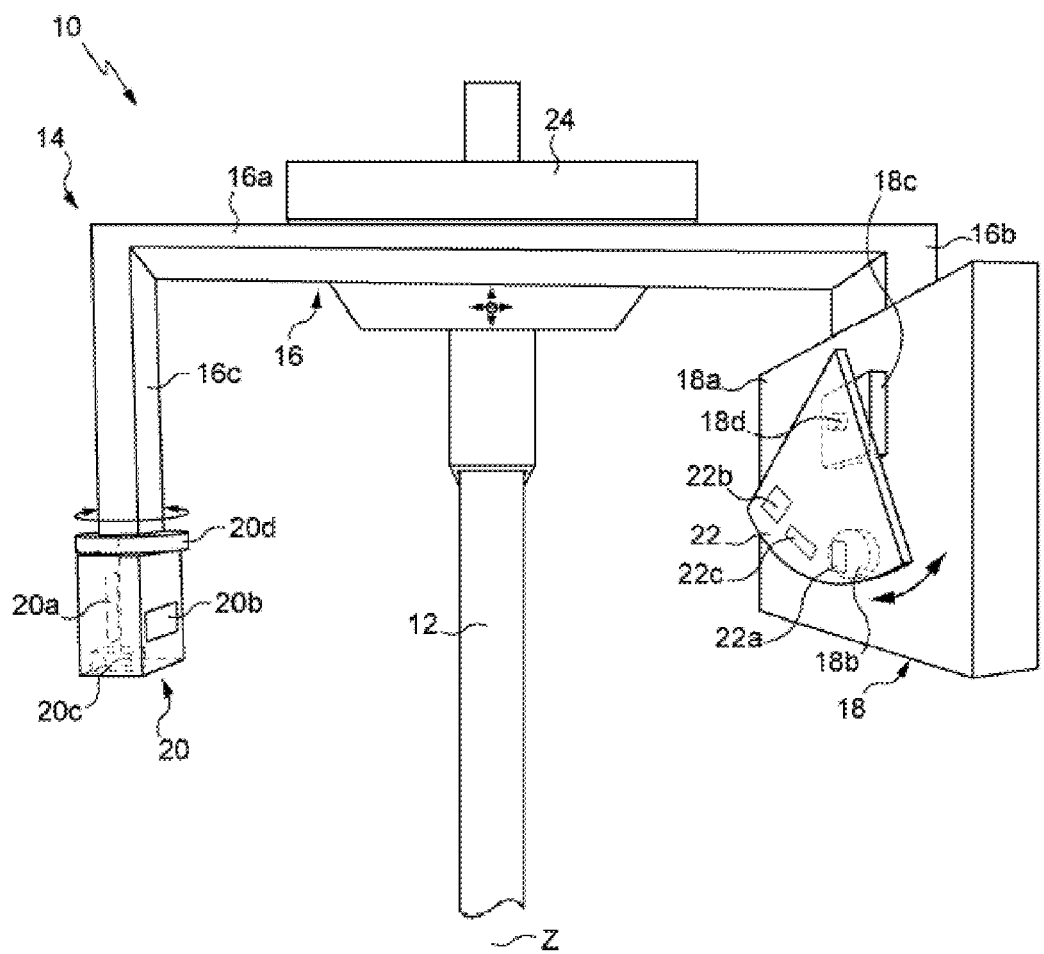
FIG. 1 is a general schematic view of a dental radiology apparatus according to the invention.
Figure 6A:
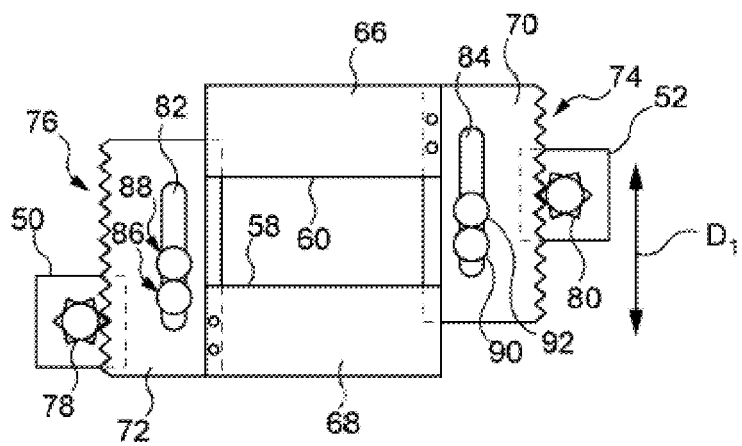
Figure 6B:
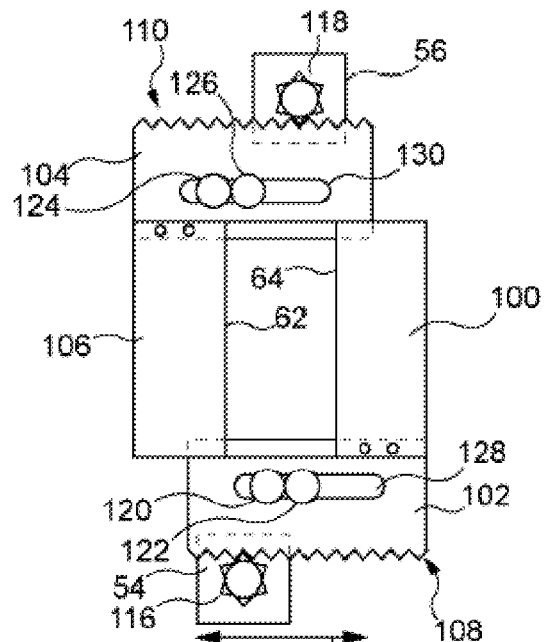
Figure 6C:
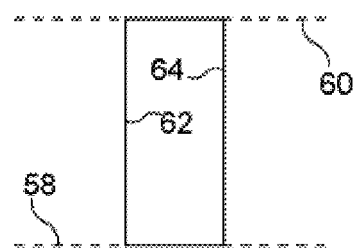
Figure 7:
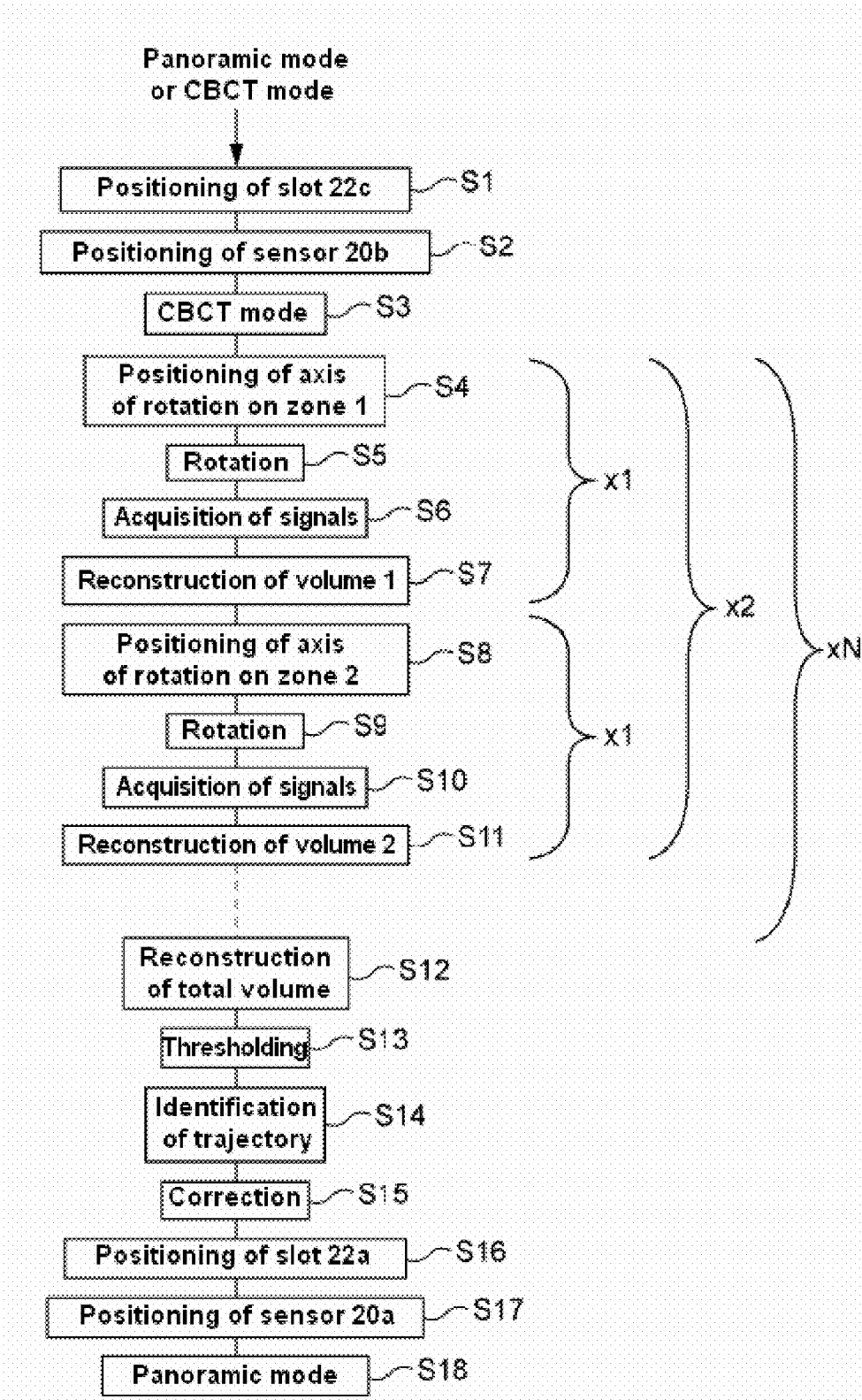
Figure 8:
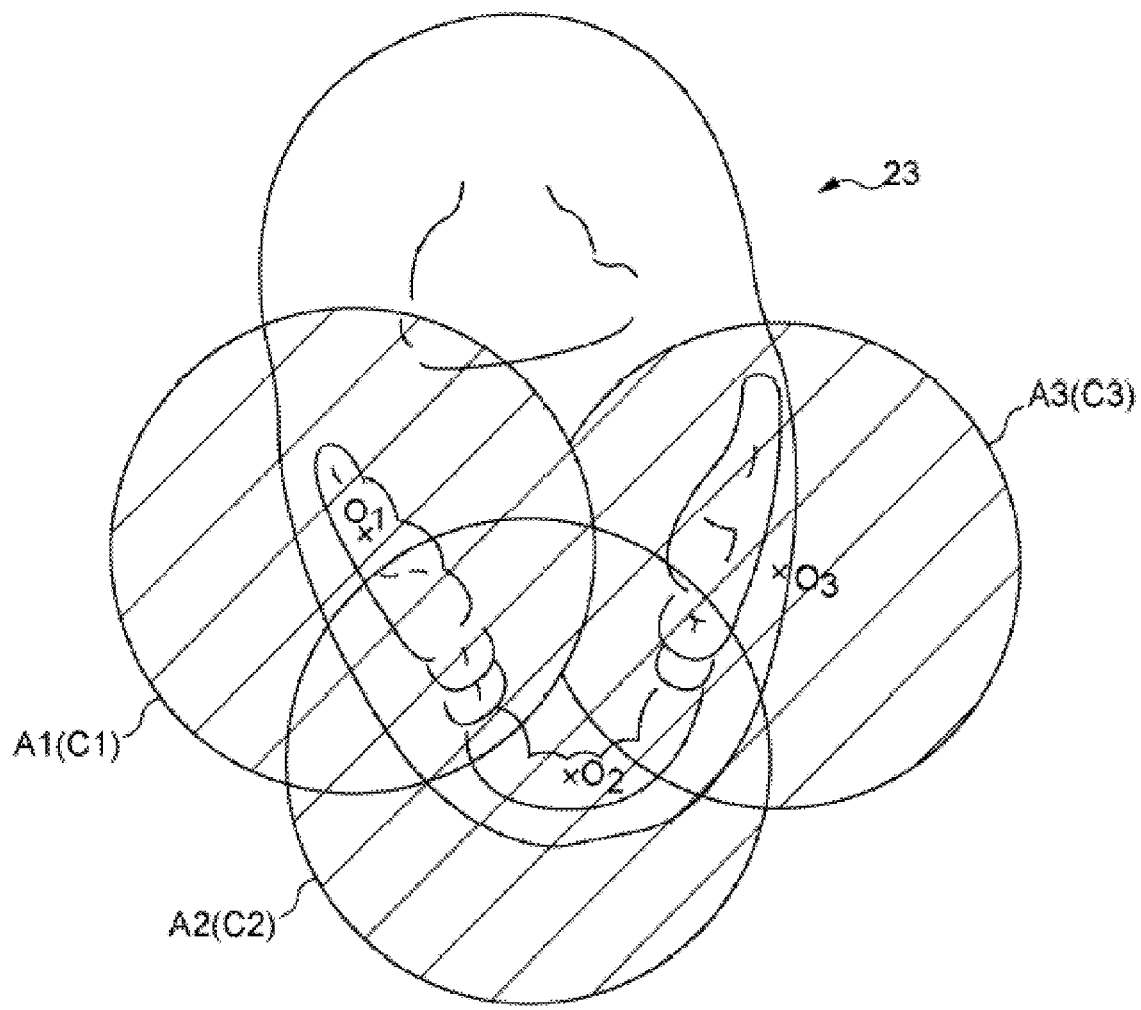
Figure 9:
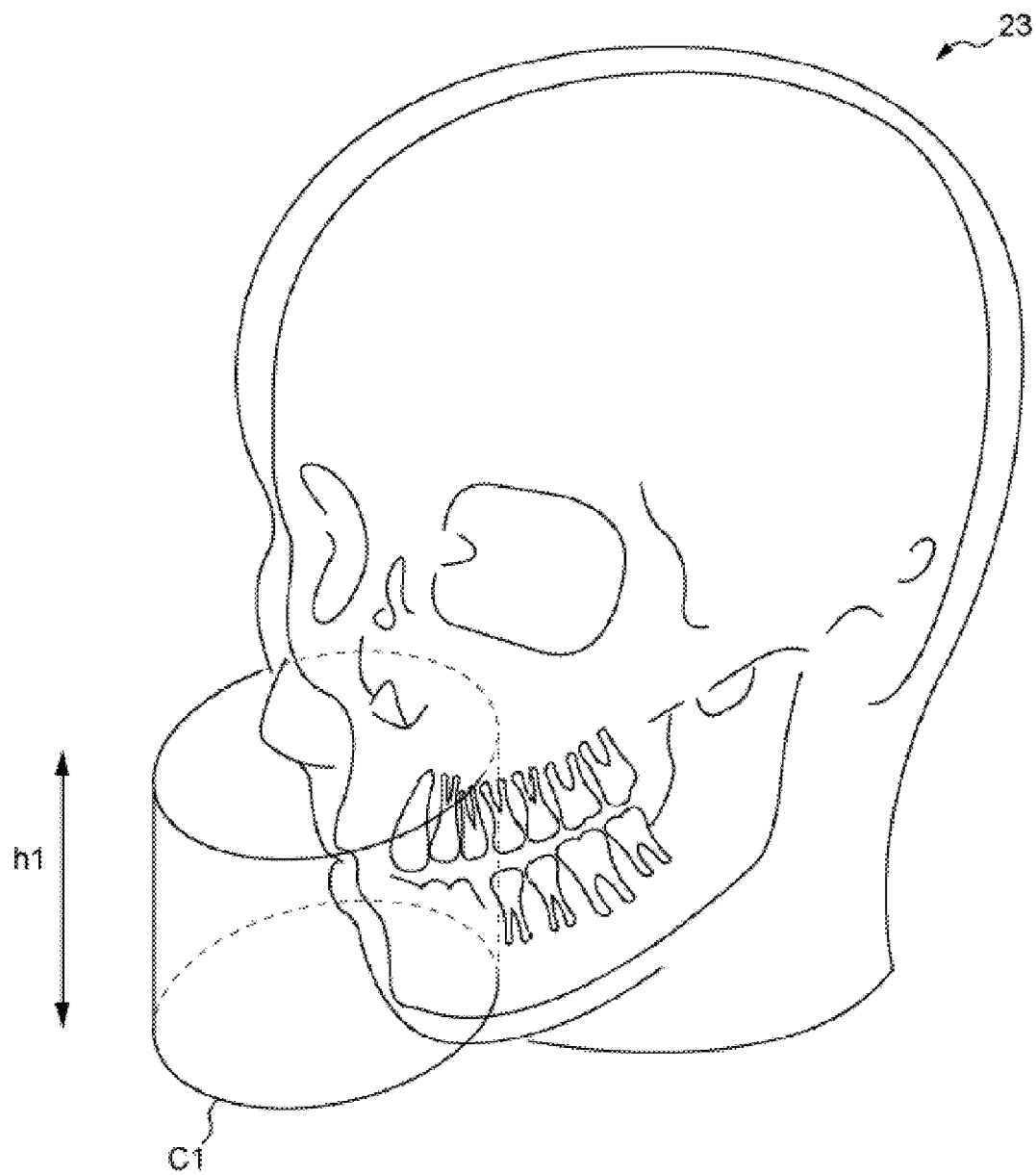
Figure 10:
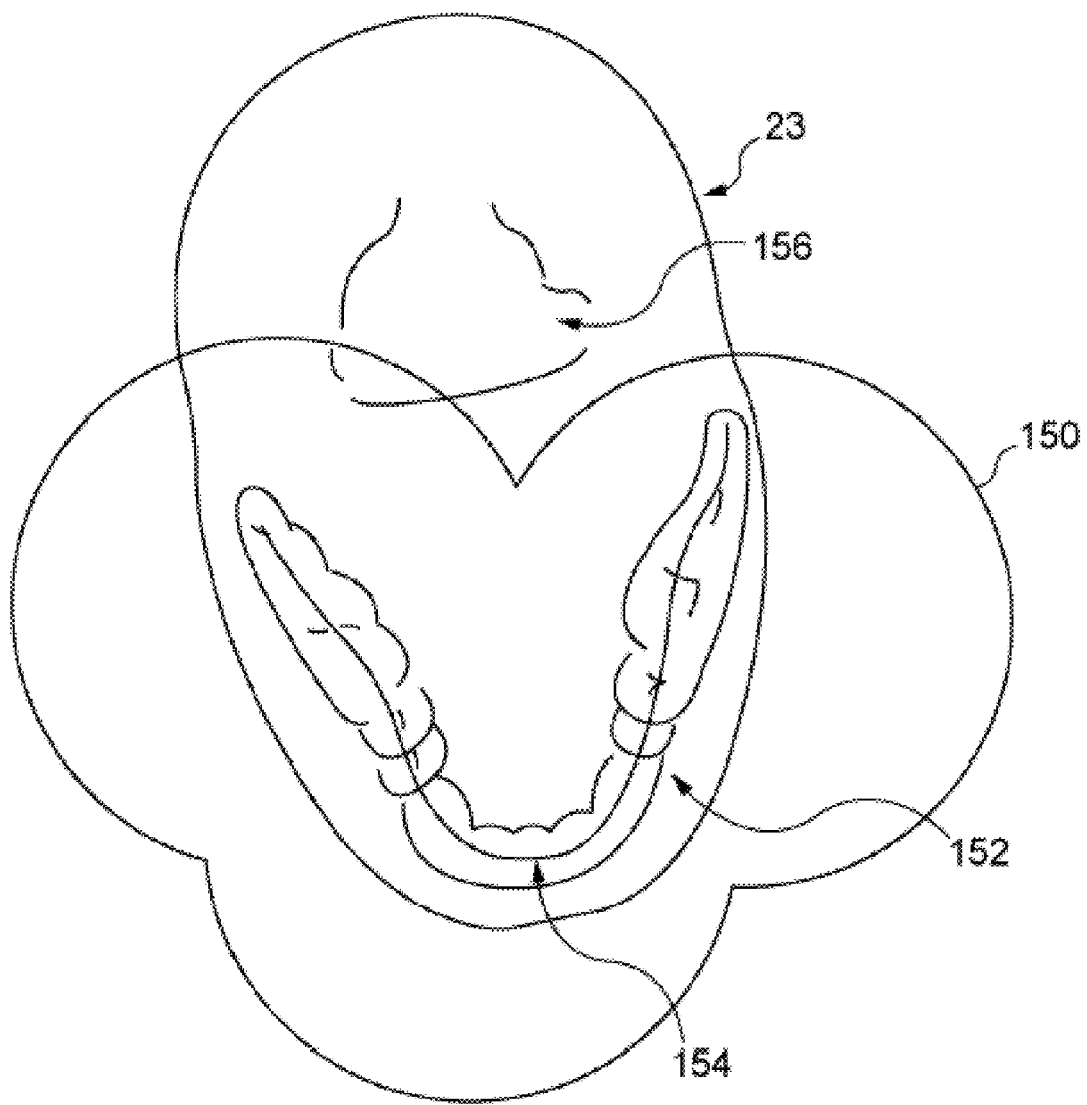
Figure 11:
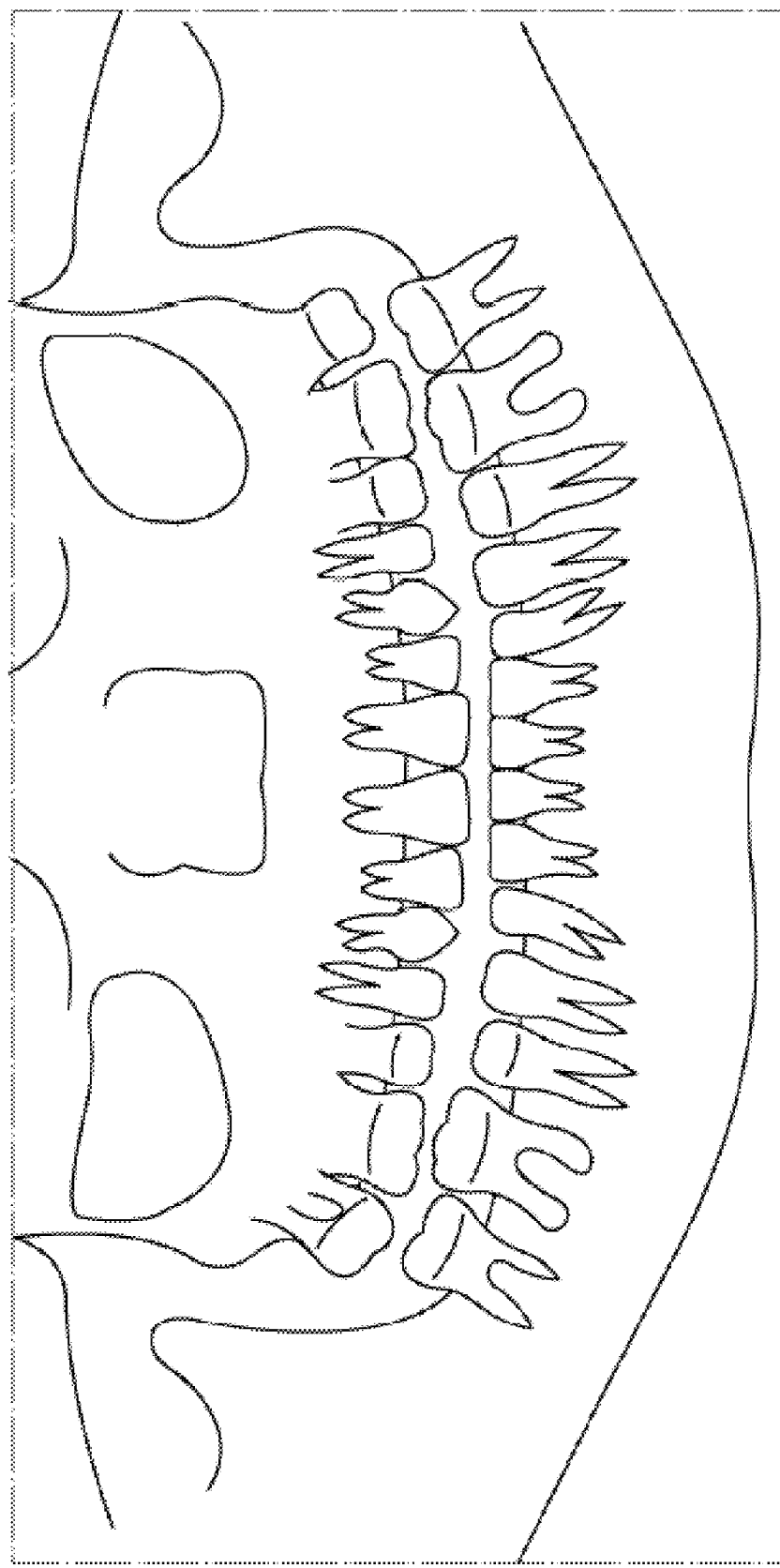

FIGS. 6a and 6b schematically illustrate the means used to create a variable-geometry slit;

FIG. 6c illustrates an example of a slit obtained with the arrangements of FIGS. 6a and 6b;

FIG. 7 represents an operating algorithm of the apparatus of FIG. 1;

FIG. 8 schematically illustrates from above three reconstructed solid portions of three different parts of a dental arch;

FIG. 9 schematically illustrates in perspective one of the reconstructed solid portions;

FIG. 10 schematically illustrates from above the dental arch, the reconstructed volume and the trajectory determined using the invention;

FIG. 11 is a schematic representation of a panoramic image obtained from the trajectory of FIG. 10.

As represented in FIG. 1 and designated by the general reference number 10, a dental radiology apparatus according to the invention is an apparatus combining at once the functionalities of a panoramic apparatus and those of a tomographic apparatus. More particularly, this apparatus allows the production of panoramic images of an object such as a dental arch as well as three-dimensional images of an object obtained by cone beam tomography. The apparatus comprises a fixed column 12, for example a vertical support tube, on which a revolving radiographic unit 14 is mounted which will now be described.

This unit comprises a mobile structure 16 in the form of a flattened C (arch) comprising a horizontal central beam 16a forming a support which constitutes the body of the C and two vertical arms 16b and 16c descending from the horizontal beam and each constituting the two branches of the C.

An X-ray source or generator 18 is mounted in fixed manner on the arm 16b, while a mobile detection unit 20 is mounted on the arm 16c.

The generator 18 and the detection unit 20 are thus arranged opposite each other and are in a fixed geometric relation to each other.

The structure 16 which acts as a support for the generator 18 and for the unit 20 constitutes the core of the revolving radiographic unit 14.

The radiology apparatus 10 also comprises, in a manner not represented, a lower arm fixed at one end to the column 12. The free end of the arm is equipped with a positioning device allowing the patient's head to be immobilized while radiographic photographs are taken, during the operation of the apparatus. The head is thus interposed between the generator 18 and the detection unit 20.

The radiation generator is equipped with a mobile support 22, for example in the form of a portion of a circle (angular sector), fitted against the side 18a of the generator which faces the unit 20 and in which an opening 18b is made for the emergence of the X-rays from the generator.

The support is positioned in front of this exit window 18b for the X-rays and comprises several collimation slits, for example three. These slits are intended to each be placed facing the emission window 18b according to the controlled displacement of the support.

A displacement means such as a motor 18c allows the displacement of the support which takes place, here in the form of a pivoting about an axis 18d perpendicular to the face 18a of the generator, to be controlled.

Thus, the controlled displacement of the support allows the positioning, in front of the window 18b, from a home position, of a collimation slit which will have been selected beforehand.

More particularly, the slits support 22 comprises three different forms of slits 22a, 22b and 22c which are each suitable for a particular mode of use or position of the apparatus when they are arranged in turn in front of an emission window 18b.

A first slit 22a is elongated along a Z-axis, for example vertical, which is perpendicular to a plane P, for example horizontal, when it is brought opposite the window 18b by the positioning means (FIG. 1).

This slit is for example rectangular in shape.

The slit 22a is used in a first position of the apparatus to produce a panoramic image of an object placed between the generator provided with this slit and the mobile detection unit 20.

The X-ray beam that has come from the emission window 18b is collimated by the slit and thus has the form of a truncated cone. This beam is elongated, at its base (in a section parallel to the plane of the slit), in a direction corresponding to the direction of elongation of the slit.

The detection unit 20 then receives the collimated radiation which has passed through the object placed on the trajectory of the radiation.

In this respect, the detection unit 20 comprises two sensors 20a, 20b and an electronics unit 20c controlling and feeding the sensors and processing the signals collected by them.

The electronics unit is common to the two sensors but comprises specific functionalities for each sensor in particular as regards the processing of the data collected by the sensors and their transmission to a remote processing unit which is not represented.

Depending on the nature of the sensors, the part of the electronics unit relating to control and/or to feeding is or is not specific to each sensor.

The first sensor, numbered 20a, is intended to cooperate, through its image acquisition surface (active optical radiation detection surface) called first image acquisition surface, with the first slit 22a in the first mode of use of the apparatus.

To do this, the apparatus comprises means of positioning the sensor 20a opposite the first slit 22a.

These means are, for example, carried by the arm 16c and are, for example, in the form of a commutator motor 20d.

This motor, when it is controlled in suitable manner, allows the unit 20 to be rotated about a vertical axis in one of the directions indicated by the double arrow in FIG. 1 and thus bring one or other of the sensors opposite the mobile support 22 and in particular the slit 22a.

This first mode of operation of the apparatus will be described in more detail with reference to FIG. 2.

A second form of slit 22b made in the support 22 is brought into correspondence with the window 18b by the positioning means 18c in a second position of the apparatus.

Correspondingly, the positioning means 20d pivot the detection unit 20 in order to bring the second sensor 20b opposite the second slit 22b (position illustrated in FIG. 1).

The second sensor is intended to cooperate, through its image acquisition surface (active optical radiation detection surface) called second image acquisition surface, with the second slit.

It will be noted that this second slit has dimensions which are suitable for those of the second sensor taking account of the distance separating the slit and the sensor, in order to be able to acquire, for example, a volumetric image of a desired object.

This second mode of operation of the apparatus (cone beam tomography) will be described in more detail with reference to FIG. 4.

Figure 2:
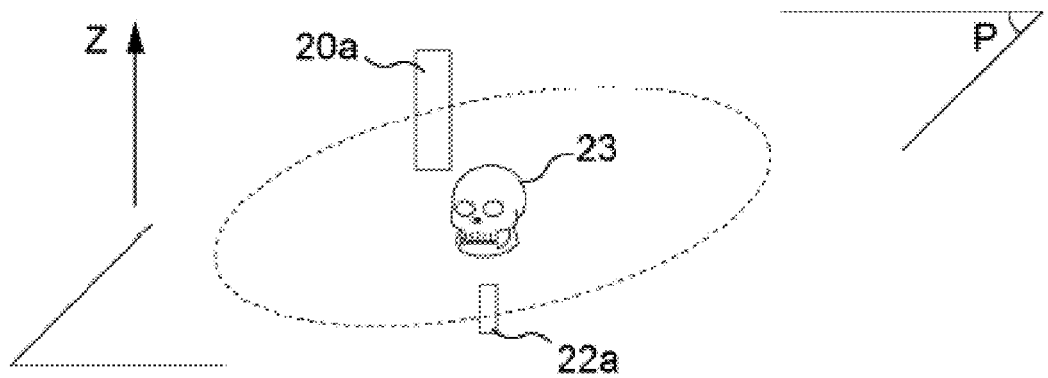
FIG. 2 is a general schematic view showing the arrangement of a first image acquisition surface and of a first form of vertical slit in position for the panoramic mode of operation.
Figure 4:
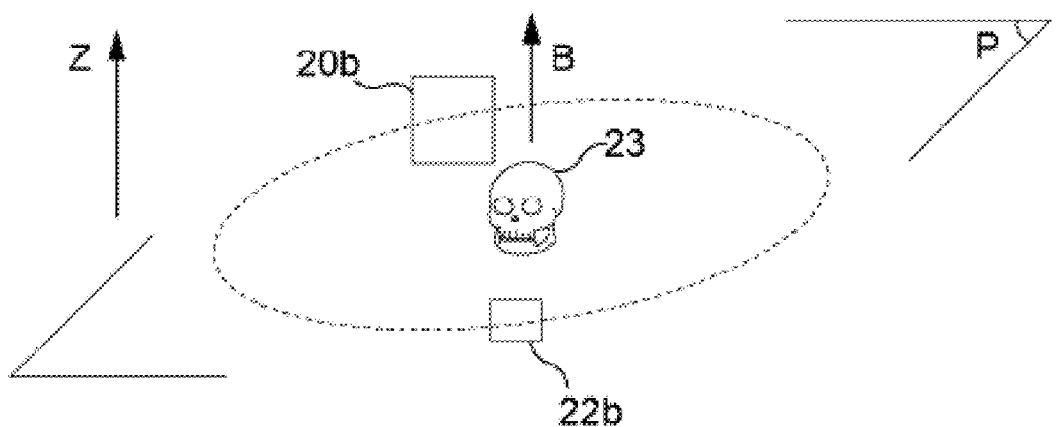
FIG. 4 is a general schematic view showing the arrangement of a second image acquisition surface and of a second form of slit for the tomographic mode of operation.

The second slit and the second sensor illustrated in FIG. 4 both have squarer shapes than those illustrated in FIG. 2.

According to a variant, the dimensions of the second sensor and of the second slit allow the acquisition by cone beam tomography of a complete jaw, even a complete skull of a person.

The support 22 also comprises a third form of collimation slit 22c which, when it is positioned in front of the emission window 18b, is elongated along an axis or in a direction parallel to the plane P which, here, for example is horizontal.

This slit is, for example, rectangular in shape.

The slit 22c is used in a third position of the apparatus in combination with the second sensor 20b of the second mode.

This third mode of operation of the apparatus (trajectory-determination mode) will be described in more detail with reference to FIG. 5.

In the position represented in FIG. 1, the first slit 22a which is elongated along the Z-axis has been selected (first mode of operation of the generator).

As represented very schematically in FIG. 2, the first sensor 20a is positioned opposite the generator 18. The first sensor is able, on the one hand, to receive the X-radiation originating from the generator that has illuminated the object 23 placed between generator and sensor and, on the other hand, to transform this radiation, attenuated by its passage through the object, into an electrical signal representing a radiographic image of this object.

It will be noted that the first sensor 20a comprises an array of pixels which is elongated in a longitudinal direction parallel to the Z-axis and brought into correspondence with the beam that has come from the collimation slit 22a for this first mode of operation of the apparatus.

This sensor is, for example, a charge transfer sensor of CCD type and its rectangular dimensions are for example 12 cm (height along the Z-axis)×1 cm (width).

The sensor and the slit have an enlargement ratio relative to each other of for example 5. Thus, if the sensor is 1 cm wide, the slit is 2 mm wide.

It will be noted that the ratio of the dimensions between the slit and the zone of the sensor that it is wished to illuminate is equal to the ratio of the distances between the focal point of emission of the X-rays and the slit (distance for example 12 cm), on the one hand, and the focal point of emission and the sensor (distance for example 60 cm) on the other.

The apparatus of FIG. 1 is able to operate in known manner in panoramic mode (first mode).

To do this, the assembly comprising the generator equipped with the first form of slit 22a and the first sensor carried by the arch-shaped structure carries out a displacement in a plane P perpendicular to the Z-axis (FIG. 2). The operation of the apparatus would, however, be identical if the Z-axis and the plane P, both perpendicular, were not vertical and horizontal respectively.

The displacement in the plane P is a movement resulting from a combination of an axis of rotation parallel to the Z-axis and a displacement along a trajectory in the shape of a horseshoe which reproduces the general shape of a dental arch of a patients jaw 23.

This trajectory corresponds, in a horizontal plane, to the median line between the two opposite edges of the dental arch.

The displacement of the generator-sensor assembly is carried out by means of displacement of the load-bearing structure.

These means are, for example, in the form of an X,Y-controlled displacement table 24 (servo-control mechanism) which is programmed to describe the aforementioned trajectory (FIG. 1).

Figure 3:
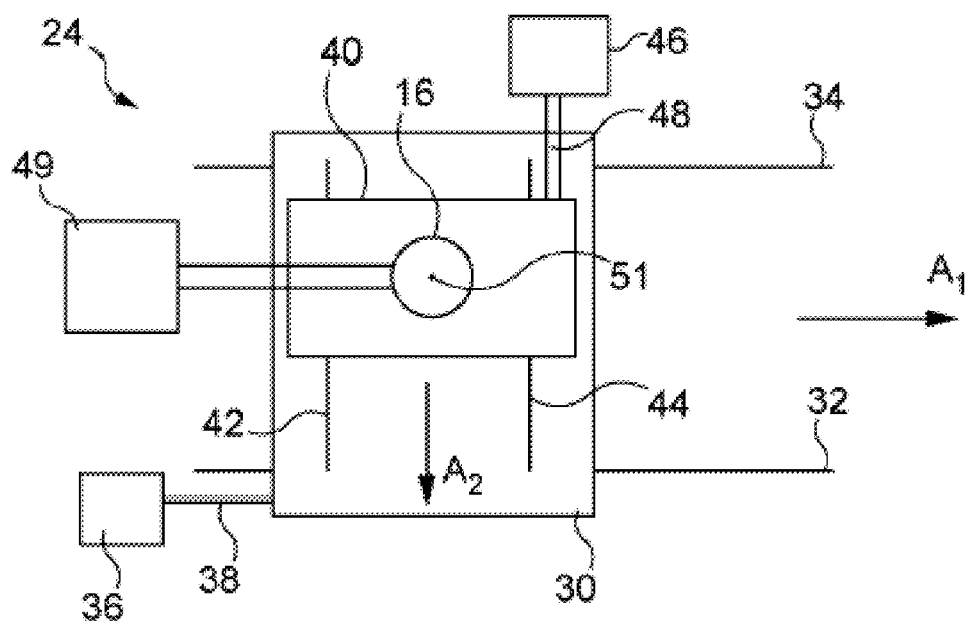
FIG. 3 is a simplified general schematic view of the displacement table 24 of the apparatus of FIG. 1.

As represented very schematically in FIG. 3, the table 24 comprises a first carriage 30 sliding on two longitudinal rails 32, 34 in a first direction A1 (Y) under the action of a first drive means such as a motor 36 connected to the carriage by an endless screw 38.

The table also comprises a second carriage 40 sliding on two longitudinal rails 42, 44 in a second direction A2 (X) (the directions A1 and A2 are contained in a plane parallel to the plane P) under the action of a second drive means such as a motor 46 connected to the carriage by an endless screw 48.

The table 24 is integral with the arch-shaped structure 16 and a drive means 49 such as a motor is connected to the structure 16 in order to drive this structure in rotation, on command, about the axis of rotation 51 perpendicular to the plane P and thus perpendicular to the plane defined by the directions A1 and A2.

By controlling the displacement of the carriages 30 and 40 in a suitable manner in the directions X and Y, the structure 16 describes the sought trajectory (in the shape of a horseshoe) in the plane P.

It will be noted that, during the displacement of the generator and first sensor 20a about the object (patients jaw) in the plane P, the sensor operates in what is called TDI ("Time Delay Integration") mode.

This purpose of this mode of operation known per se is to proceed such that the pixels of the mobile sensor which capture the radiation that has illuminated the patient's jaw are regarded as fixed in relation to the jaw.

To do this, the frequency of reading of the array of pixels is arranged such that the shift of the lines of the array towards the shift register, under the reading pulses of the latter, takes place in a direction opposite to that of the displacement of the sensor.

The TDI mode thus allows the blurring phenomena in the panoramic image obtained to be avoided.

The first mode of operation of the apparatus of FIG. 1 which has just been described relates to the panoramic mode.

The apparatus 10 according to the invention is also capable of being used in a second mode of operation to produce radiographic photographs in three dimensions by cone beam tomography.

In this mode the support 22 is displaced in order to arrange the second collimation slit 22b in front of the window 18b. Moreover, the means 20d of driving the unit 20 in rotation 20d pivot the assembly in order to bring the second sensor 20b opposite the second slit, as represented in FIG. 4.

The second sensor 20b comprises an array of CMOS pixels having a squarer shape than the first sensor and also a larger active surface.

The dimensions of the sensor are for example 6 cm (height along the Z-axis)×5 cm (width).

With such dimensions the size of the second sensor 20b is not great enough to acquire at one go the three-dimensional image (three-dimensional model) of a jaw by cone beam tomography.

For this reason, this sensor is used to produce a tomographic image of what, in dental radiology, is commonly called a "small field". This involves solely a part of interest of a jaw comprising as a minimum a dental half-arch and, for example, molars or incisors. This image is obtained by displacement, in the plane P, in rotation about an axis B parallel to the Z-axis, of the generator equipped with the second slit and the second sensor (FIG. 4).

The second slit 22b has a substantially square or rectangular shape and dimensions suitable for those of the second sensor 20b.

These dimensions are adapted in that the beam of X-rays collimated by the slit and attenuated by the object 23 must have dimensions that allow it to illuminate the whole surface of the sensor without however illuminating too large a zone around the latter.

Ideally, the dimensions of the collimated beam reaching the sensor are substantially the same as those of the latter.

The apparatus according to the invention is capable of being used in a third mode of operation in order to determine a displacement trajectory for the first panoramic mode. This trajectory will be travelled by the first sensor and the generator equipped with the first slit when the apparatus subsequently reverts to the panoramic mode of operation.

To do this, the activated drive means of the support 18c cause the support 22 to pivot by the desired angular value and in the appropriate direction of pivoting. This displacement from a home position located outside the zone in front of the window allows the third slit 22c to be brought in front of the emission window 18b (switching of the slits).

The slit 22c is thus arranged elongated in a direction contained in the plane P.

In this mode of operation, the sensor used is the second sensor 20b and is arranged opposite the slit 22c. The generator which is provided with a slit having such a spatial orientation is capable of producing an X-ray beam which is elongated, at its base, according to this same orientation.

The beam emitted with this configuration and attenuated by the jaw illuminates the active surface of the second sensor 20b.

It will be noted that such a beam illuminates only a small height of the jaw around the occlusal zone which constitutes the desired zone of interest.

The width of the beam is given by the horizontally disposed longitudinal dimension of the slit and this dimension is suitable for the width of the sensor.

This adapted longitudinal dimension of the slit allows effective use to be made of the width of the sensor.

Figure 5:
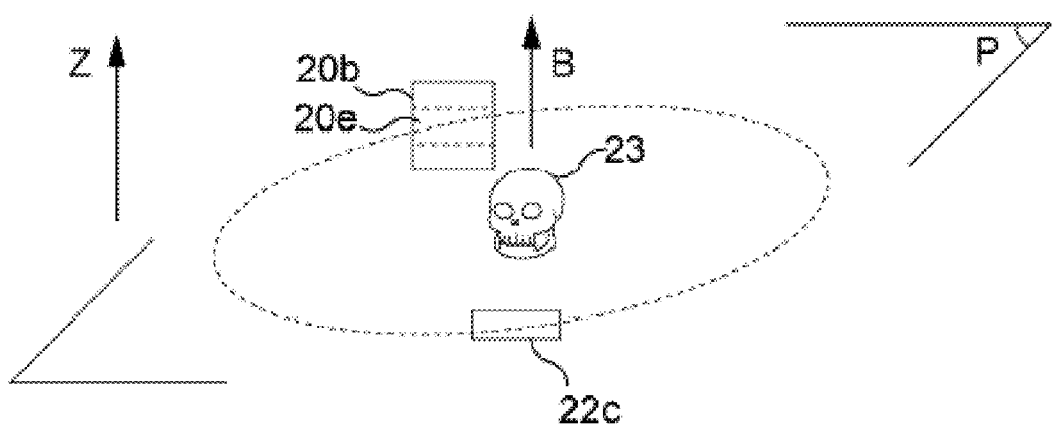
FIG. 5 is a general schematic view showing the arrangement of a third image acquisition surface and of a third form of horizontal slit in position for the mode of operation for determining a trajectory.

In FIG. 5, the illuminated zone of the second sensor has been represented by a dotted line. This zone 20e corresponds to a part of the second image acquisition surface of the sensor which has the same width as the latter but a reduced height.

The illuminated surface part is called third image acquisition surface 20e as it is this part that will collect the images data specific to the trajectory-determination mode.

The electronics unit 20c of FIG. 1 will control the reading of only the pixels comprised in this third surface.

The second sensor 20b and the third slit 22c arranged in this way (FIG. 5) will then be driven in rotation about an axis of rotation B (vertical) parallel to the Z-axis following the circle shown as a dotted line, by the means 49 of FIG. 3, in order to determine the aforementioned trajectory suitable for the object 23, as will be explained later.

It will be noted that when the size of the second sensor is great enough to acquire the 3D image of a complete jaw, even of a complete skull, the third mode described above is advantageous, as it allows a smaller radiation dose to be used to determine the trajectory.

Numerous variant embodiments are possible for the production of the different forms of slit used by the apparatus to implement the different modes.

According to a first variant, not represented, the radiology apparatus may have only two slits:
a first slit elongated in one direction which, by pivoting, serves as either the slit 22a of FIG. 1 or the slit 22c, and
a second slit analogous to the slit 22b of FIG. 1.

According to a second variant, not represented, the apparatus has two slits:
a variable-geometry slit delimited by four mobile edges and provided with independent adjustment means for the displacement of each of the edges relative to one another in order to adjust the elongation of the slit in directions perpendicular to each other, and
a second slit analogous to the slit 22b of FIG. 1.

According to a third variant, the apparatus has only one variable-geometry slit. This slit is provided with independent means of adjusting the edges of the slit in relation to one another in order to shape the desired slit to one of the forms chosen from the three slits of FIG. 1.

This third variant is illustrated in FIGS. 6a to 6c.

FIGS. 6a and 6b illustrate a variant allowing the creation of a single variable-geometry collimation slit replacing the three slits of FIG. 1.

Adjustment means are provided in order to vary, on command, the geometry of the slit and, in particular, its elongation in two directions perpendicular to each other, for example horizontal and vertical.

More particularly, the adjustment means suitable for modifying the elongation of the slit in one direction are independent of those suitable for modifying the elongation in the other direction, thus offering a greater flexibility of adjustment.

In the example illustrated, the radiology apparatus comprises four independent adjustment means 50, 52, 54, 56 for independently varying the position of each of the four edges 58, 60, 62, 64 defining the collimation slit.

The apparatus comprises a slit support for example carried by the generator 18 of FIG. 1, or even attached directly to the structure 16 (for example to the arm 16b), which is placed in front of the window 18b.

On this support are superposed, in succession, the arrangement of FIG. 6b, then that of FIG. 6a.

These arrangements have not been represented superposed here, for the sake of clarity.

More particularly, the arrangement of FIG. 6a comprises two edges 58, 60 of two plates 66, 68 positioned opposite each other (for example rectangular) which are each fixed to another plate 70, 72 respectively arranged perpendicularly.

Each pair of plates 66, 70 and 68, 72 thus forms an L or an L rotated by 180°.

The second plate 70, 72 of each pair is provided, on one of its edges opposite that against which the first plate is fixed, with a longitudinal row of teeth 74, 76.

A means of displacing the edge 58 (or 60) comprises a motor 50 (or 52) equipped on its output shaft with a toothed pinion 78 (or 80). This pinion cooperates with the teeth 76 (or 74) to trigger the displacement of the plates 72 and 68 in the direction D1 in one or other direction depending on the rotational direction of the pinion.

A guide slot 82 (or 84) is provided in the second plate 72 (or 70) and two guide pins 86, 88 (or 90, 92) integral with the aforementioned support are positioned in this groove in order to longitudinally guide the displacement of the corresponding plate and thus of the corresponding edge.

This arrangement allows, by adjusting the distance between the opposite edges 58 and 60 in the direction D1, the adjustment of one of the dimensions of the slit and thus its elongation in one direction.

In identical fashion, the arrangement illustrated in FIG. 6b allows, by adjusting the distance between the opposite edges 62 and 64 in the perpendicular direction D2, the adjustment of one of the dimensions of the slit in another direction.

Thus, by bringing the edges 62 and 64 closer together and by moving the edges 58 and 60 further apart, the slit is shaped elongated in the direction D1. A slit elongated along the Z-axis represented in FIG. 6c (like the slit 22a of FIGS. 1 and 2) is thus obtained.

On the other hand, if the edges 62 and 64 are moved further apart and the edges 58 and 60 are brought closer together, the elongated shape of the slit is produced in the direction D2. A slit elongated along an axis perpendicular to the Z-axis like the slit 22c of FIGS. 1 and 5 is thus obtained.

The slit 22b of FIGS. 1 and 4 is, for its part, obtained by moving the edges 58 and 60 away from each other, and also the edges 62 and 64, in order to give them a squarer shape than the other slits.

The different elements represented in FIG. 6b, namely the first and second plates 100, 102 (or 104, 106), the grooves 108 (or 110), the motor 54 (or 56) and its toothed pinion 116 (or 118), as well as the guide pins 120, 122 (or 124, 126) in the guide slot 128 (or 130), are identical to the corresponding elements in FIG. 6a but are shifted by only 90°.

According to a variant embodiment, not represented, the apparatus according to the invention may have only a single sensor instead of the two sensors 20a and 20b, which makes it possible to dispense with a mechanism for the displacement of the sensors.

A change of mode requires a suitable form of slit to be selected. During the image acquisition phase the pixels of the considered image acquisition surface of the sensor which will be illuminated will be read by the electronics unit 20c of FIG. 1. The non-illuminated pixels will not be read.

In this variant, the sensitive (optically active) surface of the single sensor is large enough to be able to be used in all modes of operation.

In each mode, a different image acquisition surface will be used which will represent a part of the total sensitive surface of the sensor.

Thus, in the first mode (acquisition of panoramic image), the first form of slit 22a will illuminate the first image acquisition surface of the sensor whose form is that represented in FIG. 2.

In the second mode (acquisition of volumetric image), the second form of slit 22b will illuminate the second image acquisition surface of the sensor whose form is that represented in FIG. 4.

In the third mode (determination of trajectory), the third form of slit 22c selected shapes the radiation in order that it illuminates only a part (third image acquisition surface 20e) of the second image acquisition surface whose form is represented in FIG. 5.

The apparatus 10 which has just been described comprises the means that allow it to produce panoramic images of improved quality compared with the state of the art and its different modes of operation will now be described.

FIG. 7 represents an algorithm detailing the principal steps of a method of operating/using the apparatus 10 according to the invention.

This algorithm is for example stored in a storage area of a programmable device (example: a computer of PC type) which controls the operation of the apparatus 10 and is executed on command.

This device is generally remote from the apparatus and is located several metres from it for example.

The method according to the invention can advantageously be used automatically, thus limiting human involvement.

Prior to the execution of the algorithm of the method illustrated in FIG. 7 the radiology apparatus is:
either in the first panoramic mode of operation (first sensor 20a and slit 22a in FIG. 2),
or in the second cone beam tomographic mode of operation (second sensor 20 b and slit 22b in FIG. 4) also called CBCT ("Cone Beam Computed Tomography").

The apparatus 10 thus changes mode by switching from one of these two modes to a third new mode of operation. This new mode will allow it to reliably and effectively determine a trajectory which will be travelled in the plane P by the assembly comprising generator and slit 22a and first sensor 20a for the production of a panoramic image of the patient's jaw.

To do this, the algorithm begins with a first step S1 of positioning the collimation slit 22c.

By displacing the slits support 22, the slit 22c passes from a home position located outside the radiation that has come from the generator to a position located in front of the emission window 18b.

Thus, the beam of X-rays will be collimated by this slit oriented parallel to the plane P, i.e. horizontally here.

The algorithm comprises a second step S2 of positioning the sensor 20b opposite the slit oriented in this way.

This step takes place only when the previous mode of operation of the apparatus was in panoramic mode, as otherwise the second sensor is already arranged in position (FIG. 4).

In this case, the mechanism 20d that switches the sensors switches the sensors 20a and 20b as explained previously.

After these positioning steps, the sensor and the slit are arranged as illustrated in FIG. 5.

During the following step S3 the radiology apparatus is activated in order to change to the CBCT mode of operation.

It will be noted that this third mode of operation (trajectory-determination mode) will not allow a complete radiographic photograph of the jaw to be obtained by the CBCT technique. On the other hand, this mode of operation will be used, temporarily, to acquire certain personalized data (specific to the illuminated object), not accessible in panoramic mode, which will be used subsequently in the panoramic mode.

In this mode the slit is positioned such that the collimated X-ray beam can illuminate a part of the jaw located on either side of the occlusal zone in order to acquire image data specific to this zone.

Step S3 is followed by a step S4 during which the apparatus adjusts the position of the assembly formed of the second sensor 20b and the generator provided with the third slit 22c in the plane P, about a fixed axis B parallel to the Z-axis which will serve as axis of rotation for this assembly.

In other words, the axis of rotation of this assembly is suitably positioned in relation to the volume of the object or of the part of the object to be reconstructed.

In the example described, this axis is positioned centred on a first zone A1 of the jaw (centre of the zone in O1) in order to obtain a three-dimensional model of this zone.

FIG. 8 schematically illustrates from above the dental arch and the positioning on the point O1 of the axis of rotation B of the assembly comprising sensor and generator.

This positioning is achieved using the displacement means 24 illustrated in FIG. 3 that has already been described.

During the following step S5 the assembly formed of the generator equipped with its collimation slit and the sensor is driven in rotation in the plane P, about the axis B parallel to the Z-axis. During this rotation movement, this assembly occupies a plurality of successive angular positions for each of which image signals of the object illuminated by the collimated radiation are acquired by the sensor. More particularly, the image signals are acquired by the third image acquisition surface 20e (FIG. 5) of the sensor which represents a sub array of pixels of the array of pixels of the sensor 20b.

During this movement, the centre of rotation of the assembly comprising generator and sensor is fixed.

Step S6 relates to the acquisition of data in cone beam tomographic mode of operation (CBCT) on the object (for example the object 23 of FIG. 5) placed between the generator and the sensor, and more particularly the patient's jaw.

For each angular position of this assembly, the data captured by the sensor represent a projection of the first zone of the object along the generator-image sensor axis.

It will be noted in this regard that steps S5 and S6 are simultaneous.

Thus, at the end of a complete rotation of the assembly comprising generator and sensor, there is obtained, for example, a set of image signals, each representing a projection of the first zone of the object 23 illuminated by the beam and, for example, 360 projections of this zone of the object in the case where a photograph is taken for each degree of rotation.

Each analogue image signal is captured by a sub array of pixels of the array of pixels of the sensor, transformed into an analogue electrical signal by the sensor, then converted into a digital signal by the electronics unit 20c of FIG. 1.

It will be noted that in order to reduce the dose of X-radiation used to obtain these signals, it may be advisable to use the capability of the sensor to group the pixels of the array (and thus of the submatrix) according to a predetermined number, for example in fours or nines, for the purpose of reading.

In fact, by reading the pixels for example per group of four or nine (more generally per group of pixels forming a square) depending on the chosen grouping ("binning"), the signal-to-noise ratio of the sensor is increased, thus allowing the dose of radiation to be reduced.

During the following step S7 the volume of the illuminated part of the object (first zone A1) is reconstructed in a manner known to a person skilled in the art (ex: by using FDK algorithms) from the set of image signals obtained previously and the reconstructed volume is in the form of a cylinder C1 of small height. The height h1 or thickness of the cylinder is limited by the height of the slit 22c along the Z-axis in FIG. 5 (to minimize the dose of radiation), while the diameter of the cylinder, for its part, is limited by the width of the sensor apart from enlargement ratios.

It will be noted that the height of the slit has been chosen to illuminate only a zone of small height surrounding the occlusal zone.

By way of example, the height of the cylinder ranges from a few hundreds of micrometres to a few millimetres.

The first volume C1 is represented in FIG. 9 where it partly surrounds the patient's dental arch (this volume corresponds, seen from above in FIG. 8, to the circle identified by the reference A1).

This first reconstructed volume provides a three-dimensional model of the form of a first part of the illuminated object which contains sufficient information to determine the sought data specific to this part of the object.

It will be noted that the three-dimensional model of the part of the object is vertically centred (along the Z-axis) in relation to the zone of interest. This centring is carried out when the assembly comprising generator and sensor is positioned before the assembly is rotated (step S5). The zone of interest in the example described is the "occlusal plane" of the patient's jaw, that is to say the contact interface between the teeth.

Steps S8 to S11 correspond to steps S4 to S7 respectively which have just been described except that step S8 provides for the positioning of the axis of rotation of the assembly comprising sensor and generator on the centre O2 of a second zone A2 of the jaw (FIG. 8).

In thus displacing the assembly comprising sensor and generator and carrying out steps S9 to S11, a second cylindrical volume C2 is obtained which is not represented in FIG. 9, for the sake of clarity. The second cylindrical volume is, however, indicated from above in FIG. 8 where it corresponds to the circle identified by the reference A2.

The second volume reconstructed in known manner thus provides a three-dimensional model of the form of a second part of the illuminated object which contains sufficient information to determine the sought data specific to this part of the object. This volume also contains items of information redundant with those of the first volume, as the zones overlap.

The details of the operations carried out during steps S8 to S11 are identical to those of steps S4 to S7 and thus they will not be repeated here.

It will be noted that the series of steps S4 to S11 is repeated as many times N as is necessary for the number of three-dimensional models obtained to allow the complete reconstruction of the sought object.

In this example, the series of steps is repeated three times and the cylindrical volume C3 corresponds to the circle A3 seen from above in FIG. 8 and represents another part of the jaw.

This third volume reconstructed in known manner provides a three-dimensional model of the form of the third part of the illuminated object and it, too, contains items of information redundant with the first two volumes.

The number of reconstructed volumes depends principally on the size of the second sensor 20b and in particular the third image acquisition surface 20e. The smaller the size of the sub array of pixels corresponding to the third surface, the higher this number is.

According to an advantageous variant embodiment, the acquisition of all the image signals for all the three-dimensional models (three here) is carried out before the reconstruction of the volumes begins. This allows the risks of the patient moving, if immobilized for too long, to be reduced.

Consequently, it is thus easier to reliably combine (join end-to-end) the different volumes with one another.

During the following step S12 the three-dimensional model of the jaw is reconstructed from the three-dimensional models of the N different parts of the jaw.

In particular, here N is equal to 3 and the three cylindrical volumes are combined. The set of digital data which they each contain allows the simple reconstruction of the total volume 150 illustrated from above in FIG. 10 taking account of the data common to several volumes.

This volume is delimited by the combining of the outer contour of the three volumes C1, C2 and C3 and thus has the appearance, seen from above (FIG. 10), of a three-leaf clover.

It will be noted that, during the acquisition of the data constituting the volumes C1 to C3 (FIG. 8), it is advantageous to start by acquiring the data relating to the cylinder centred on the zone of the incisors. This cylinder will then be used as reference for the combining with the other cylinders, as it is in the zone where the incisors are located that the thickness of the cutting plane is finest, and thus most susceptible to errors.

It should be noted that the use of known algorithms for end-to-end joining/connecting of volumes (combining of volumes) based, for example, on the identification of points common to all these volumes, is not necessary in all cases.

This is so in particular when:
the acquisitions of the image signals of all the volumes to be reconstructed are carried out one after the other, and
a support system immobilizes the patient while the photographs are taken.

In fact, in so far as, according to the invention, the information used to locate the trajectory after the volumes have been joined end-to-end is only qualitative, an error in the millimetre range in the end-to-end joining of the volumes, and thus of the trajectory, is virtually of no consequence for the invention.

During the following step S13 the object or the part of the object of interest, namely in this case the patient's dental arch, is defined from the volume reconstructed in this way.

To do this, what is called a "thresholding" or "segmentation" operation is carried out on the data in the reconstructed volume.

The procedure continues, for example by thresholding, by analyzing the differences in the shades of grey between the teeth and their environment which represent differences in density and the shape of the dental arch is deduced from it in three dimensions.

The shape of the dental arch 152 is thus obtained, as represented from above in FIG. 10 in which the envelope of the reconstituted volume 150 is also indicated.

By extracting horizontal sections from the shape of the dental arch 152, the procedure continues during the following step S14 with the determination of the median line 154 which extends, in the dental arch, seen from above, between the opposite edges of this.

The determination of this median line corresponds to the identification of a "trajectory".

More particularly, this median line 154 (FIG. 10) will be used subsequently, when the apparatus will operate in panoramic mode, as a trajectory which the generator provided with the first slit 22a and the first sensor will travel in order to obtain a panoramic image of the object (arrangement of FIG. 2).

This trajectory in the shape of a horseshoe will allow the panoramic apparatus 10 to be programmed, in a manner matched and personalized to the object. The panoramic apparatuses according to the prior art operate from standard forms of dental arch which are therefore not suitable for the object to be radiographed and are not very precise, unlike the invention.

It will be noted that the thresholding step forms part of the determination of the trajectory.

The trajectory identified in step S14 is sometimes disturbed by different phenomena (metal artefacts such as fillings which are likely to give rise to star-shaped noise around the metal objects, presence of other objects in the field such as the vertebral column 156 in FIG. 10).

In order to improve the accuracy of the trajectory obtained in step S14, a step S15 (optional) correcting this trajectory, for example by smoothing, is provided for.

When the corrected trajectory has been obtained, the following step S16 is carried out. During this step the apparatus positions the first collimation slit 22a in front of the emission window 18b by pivoting of the support 22 by the appropriate angle, and in the desired direction of rotation.

Likewise, during step S17, the apparatus carries out a switching of the sensors in order to bring the first sensor 20a opposite the first slit 22a. The arrangement of the sensor and of the slit of the generator is that of FIG. 2 that has already been described.

After these positioning steps, the panoramic apparatus can thus be programmed anew to operate in panoramic mode during a step S18.

On this occasion, the trajectory obtained in step S14, optionally corrected in step S15, is used to program the displacement of the assembly formed of the generator provided with the collimation slit and the sensor that have been newly positioned parallel to the Z-axis.

During the operation of the apparatus in parameterized panoramic mode with a more suitable trajectory than in the prior art, the assembly formed of the generator and the sensor carries out a rotation movement about its vertical axis of rotation which also moves in a controlled manner along this trajectory using the different drive means illustrated in FIG. 3.

During this displacement, the vertically positioned sensor, operating in TDI mode as explained above, acquires image data of the object (here the arch) illuminated by the radiation which produce the sought panoramic image.

In known manner, a panoramic image of the arch is obtained from the image data acquired by the sensor during the displacement along the trajectory in the shape of a horseshoe.

By combining the movements of rotation of the arch 16, displacement of the centre of rotation of the arch using the displacement table 24, sliding of the pixels of the sensor (TDI mode), a virtual rotation point is recreated which is contained at any time in the focal trough. Thus, the anatomical structures located outside this manifest themselves in a streaking which does not harm the diagnosis, and the structures contained in the focal trough appear clear.

FIG. 11 illustrates schematically the panoramic image obtained according to the invention.

It will be noted that the panoramic image obtained in this way has an optimized quality compared with the techniques known according to the prior art, since the panoramic image is here perfectly matched to the object, in this case the morphology of the patient's jaw.

Moreover, the method which has just been described avoids numerous manoeuvres by the operator, manoeuvres which moreover manifest themselves in inaccurate results.

It will be noted that when the apparatus is operating in trajectory-determination mode the aim is not to obtain a high-quality image using this mode. It is for this reason that the dose of radiation can be reduced in this mode of operation.

It should be noted that the algorithm of FIG. 7 is not limited to the use with the apparatus of FIG. 1.

In fact, this algorithm can be used with apparatuses having different configurations, such as, for example, those of the embodiments described above, optionally combined with one another.

Thus, the apparatus can have a variable-geometry slit instead of the switching device of FIG. 1.

Moreover, the apparatus can have only a single sensor instead of two. In this case, the sensor-changing steps S2 and S17 in the algorithm of FIG. 7 are not necessary. With a single sensor, the apparatus can have one variable-geometry slit or several slits.

The invention claimed is:
1. Dental radiology apparatus comprising:
a generator (18) provided with a window (18b) emitting X-radiation and a collimation device positioned in front of said window in order to collimate the radiation in a suitable manner using several forms of collimation slits,
at least one sensor (20a, 20b) comprising a first image acquisition surface elongated along a Z-axis perpendicular to a plane P and being used in a first position of the apparatus to produce a panoramic image of a jaw placed between the generator and the first image acquisition surface, the panoramic image being produced from the X-radiation collimated by a first form of collimation slit (22a) elongated along the Z-axis and received by the first sensor image acquisition surface and by displacement of the generator and of said first surface along a given trajectory in the plane P combined with a rotation about an axis parallel to the Z-axis, the said at least one sensor comprising a second image acquisition surface used in cone beam tomographic mode, in a second position of the apparatus, to produce a three-dimensional model of only a part of the jaw from the X-radiation collimated by a second form of collimation slit (22b) and received by the second image acquisition surface and by displacement of the generator and of said second surface in rotation about an axis parallel to the Z-axis, the second form of collimation slit having dimensions matched to those of the second image acquisition surface, characterized in that the apparatus is able to occupy a third position of use and to this end comprises means of positioning, in front of the window emitting X-radiation, a third form of collimation slit (22c) elongated in a direction parallel to the plane P and arranged opposite a third image acquisition surface corresponding to a part of the second surface along the Z-axis in order to cooperate with the third image acquisition surface, the longitudinal dimension of the slit in the direction parallel to the plane P being matched to the dimension of the second image acquisition surface in this same direction.

2. Apparatus according to claim 1, characterized in that it comprises means of obtaining in cone beam tomographic mode a predetermined number of three-dimensional models each representing a different part of the jaw from an assembly comprising third image acquisition surface and generator provided with the third form of collimation slit elongated parallel to the plane P.

3. Apparatus according to claim 2, characterized in that each first, second and third image acquisition surface of the said at least one sensor is an array of pixels or a sub array of pixels, and the predetermined number of three-dimensional models depends in particular on the size of the array or the sub array of pixels of the third image acquisition surface.

4. Apparatus according to claim 1, characterized in that it comprises:
means of positioning, in the plane P, about a fixed axis parallel to the Z-axis, the assembly comprising third image acquisition surface and generator provided with the third form of collimation slit elongated parallel to the plane P;
means of driving in rotation, about the fixed axis of rotation, the assembly comprising third surface and generator;
means of acquiring several image signals of a part of a jaw illuminated by the radiation collimated by the third form of slit oriented parallel to the plane P for a plurality of angular positions occupied by the assembly comprising third surface and generator during the rotation movement.

5. Apparatus according to claim 4, characterized in that the positioning means are able to position the assembly comprising third image acquisition surface and generator provided with the third form of collimation slit elongated parallel to the plane P successively about other fixed axes of rotation in order that, for each positioning about one of these other axes of rotation, the drive means and the acquisition means are able to cooperate with a view to acquiring image signals of another illuminated part of the jaw.

6. Apparatus according to claim 4, characterized in that it comprises means of obtaining a three-dimensional model of each illuminated part of a jaw from the set of acquired image signals.

7. Apparatus according to claim 6, characterized in that it comprises:
means of reconstructing a three-dimensional model of a jaw from the three-dimensional models of the different parts of a jaw; and
means of identifying, from the three-dimensional model reconstructed in this way, a trajectory which the assembly comprising first image acquisition surface and generator will have to follow during the subsequent production of a panoramic image of the jaw.

8. Apparatus according to claim 7, characterized in that the means of identifying a trajectory from the reconstructed three-dimensional model comprise means of thresholding or segmenting the data constituting this three-dimensional model.

9. Apparatus according to claim 4, characterized in that each first, second and third image acquisition surface of the said at least one sensor is an array of pixels or a sub array of pixels, and the means of acquiring several image signals comprise means of reading the data captured by the array or the sub array of pixels, said reading means comprising means of grouping the pixels according to a predetermined number of pixels for the purpose of reading the pixels grouped in this way.

10. Apparatus according to claim 1, characterized in that the collimation device comprises three collimation slits of different forms which are each able to be positioned, on command, in front of the emission window in order to collimate the radiation in an appropriate manner.

11. Apparatus according to claim 1, characterized in that the collimation device comprises a mobile collimation slits support which is able to position, under the action of positioning means, a form of collimation slit in front of the window emitting X-radiation.

12. Apparatus according to claim 11, characterized in that the collimation slits support is able to pivot under the action of the positioning means.

13. Apparatus according to claim 1, characterized in that the collimation device comprises a collimation slit and means of adjusting the dimensions of the slit in order to give it at least some of the three forms of collimation slit used in the three respective positions of the apparatus.

14. Apparatus according to claim 13, characterized in that the adjustment means are means of adjusting the elongation of the slit in directions perpendicular to each other.

15. Apparatus according to claim 14, characterized in that the adjustment means are independent as regards the directions.

16. Apparatus according to claim 1, characterized in that the collimation slit is delimited by four edges (58, 60, 62, 64) and the adjustment means are able to displace each of the edges independently of one another.

17. Apparatus according to claim 1, characterized in that each first, second and third image acquisition surface of the said at least one sensor is an array of pixels or a sub array of pixels.

18. Apparatus according to claim 1, characterized in that the first and second image acquisition surfaces form part of a first and a second sensor respectively.

19. Apparatus according to claim 18, characterized in that it comprises a mobile unit (20) comprising the two sensors and which is able to position, on command, opposite the generator, each of the two sensors in order that it receives the X-radiation collimated by a collimation slit of appropriate form.

20. Apparatus according to claim 1, characterized in that the first, second and third image acquisition surfaces form part of a single sensor.

21. Method for producing a panoramic image of a patient's jaw from a dental radiology apparatus comprising:
- a generator (18) provided with a window (18b) emitting X-radiation and a collimation device positioned in front of said window in order to collimate the radiation in a suitable manner using several forms of collimation slits,
- at least one sensor (20a, 20b) comprising a first image acquisition surface elongated along a Z-axis perpendicular to a plane P and being used in a first position of the apparatus to produce a panoramic image of a jaw placed between the generator and the first image acquisition surface, the panoramic image being produced from the X-radiation collimated by a first form of collimation slit (22a) elongated along the Z-axis and received by the first sensor image acquisition surface and by displacement of the generator and of said first surface along a given trajectory in the plane P combined with a rotation about an axis parallel to the Z-axis, the said at least one sensor comprising a second image acquisition surface used in cone beam tomographic mode, in a second position of the apparatus, to produce a three-dimensional model of only a part of the jaw from the X-radiation collimated by a second form of collimation slit (22b) and received by the second image acquisition surface and by displacement of the generator and of said second surface in rotation about an axis parallel to the Z-axis, the second form of collimation slit having dimensions matched to those of the second image acquisition surface, characterized in that the method comprises, in a third position of use of the apparatus in cone beam tomographic mode, the following preliminary steps in order to obtain a trajectory which will be travelled in the plane P, by the assembly comprising generator and first image acquisition surface, in the first position of use of the apparatus for the production of a panoramic image of the jaw:
  - positioning (S1), in front of the window emitting X-radiation, of a third form of collimation slit (22c) elongated in a direction parallel to the plane P and the longitudinal dimension of which in this direction is matched to the dimension of the second image acquisition surface in this same direction,
  - positioning (S2), opposite the third form of collimation slit oriented in this way, of a third image acquisition surface corresponding to a part of the second surface along the Z-axis, for the purpose of cooperation of the third form of slit and the third surface.

22. Method according to claim 21, characterized in that it comprises, following the positioning steps, a step of obtaining in cone beam tomographic mode a predetermined number of solid images each representing a different part of a jaw from the assembly comprising third image acquisition surface and generator provided with the third form of collimation slit elongated parallel to the plane P.

23. Method according to claim 22, characterized in that each first, second and third image acquisition surface of the said at least one sensor is an array of pixels or a sub array of pixels, and the predetermined number of three-dimensional models depends in particular on the size of the array or the sub array of pixels of the third image acquisition surface.

24. Method according to claim 21, characterized in that it comprises the following steps:
- a) positioning (S4) in the plane P, about a fixed axis parallel to the Z-axis, of the assembly comprising third image acquisition surface and generator provided with the third form of collimation slit elongated parallel to the plane P;
- b) driving in rotation (S5) of the assembly comprising third image acquisition surface and generator about the fixed axis of rotation;
- c) acquisition (S6) of several image signals of a part of a jaw illuminated by the radiation collimated by the third form of slit oriented parallel to the plane P for a plurality of angular positions occupied by the assembly comprising third image acquisition surface and generator during the rotation movement.

25. Method according to claim 24, characterized in that it comprises the following steps:
- positioning of the assembly comprising third image acquisition surface and generator provided with the third form of collimation slit elongated parallel to the plane P about another fixed axis parallel to the Z-axis and
- realization of steps b) and c) for the acquisition of the image signals of another illuminated part of the jaw.

26. Method according to claim 24, characterized in that it comprises a step of obtaining, from the set of acquired image signals, a three-dimensional model of each illuminated part of the jaw.

27. Method according to claim 26, characterized in that it comprises the following steps:
- reconstruction (S12) of a three-dimensional model of a jaw from the three-dimensional models of different parts of a jaw;
- identification (S14), from the three-dimensional model reconstructed in this way, of a trajectory which the assembly comprising first image acquisition surface and generator will have to follow during the subsequent production of a panoramic image of the jaw.

28. Method according to claim 27, characterized in that the identification of a trajectory from the reconstructed three-dimensional model comprises a step (S13) of thresholding or segmenting the data constituting this three-dimensional model.

29. Method according to claim 24, characterized in that each first, second and third image acquisition surface of the said at least one sensor is an array of pixels or a sub array of pixels, and the acquisition of several image signals comprises a step of reading the data captured by the array or the sub array of pixels which comprises a grouping of the pixels according to a predetermined number of pixels for the purpose of reading the pixels grouped in this way.

30. Method according to claim 21, characterized in that it comprises the following steps:
- positioning (S16), in front of the window emitting X-radiation, of the first form of collimation slit elongated along the Z-axis,
- positioning (S17) of the first image acquisition surface opposite the first form of collimation slit oriented in this way,
- control of the displacement of the assembly formed of the generator provided with the first form of collimation slit and the first image acquisition surface arranged parallel to the axis (Z) along the trajectory previously obtained combined with a rotation movement about an axis parallel to the axis (Z), acquisition of a panoramic image of the jaw during this controlled displacement combined with a shift of the pixels of the first image acquisition surface.

31. Method according to claim 21, characterized in that the collimation device comprises three collimation slits of different forms and the positioning of each of them in front of the emission window is carried out by displacement from a home position placed outside the radiation that has come from the generator.

32. Method according to claim 21, characterized in that the collimation device comprises a collimation slit and the positioning, in front of the emission window, of a different form of collimation slit is carried out by adjusting the dimensions of the slit.

33. Method according to claim 32, characterized in that the adjustment more particularly comprises the adjustment of the elongation of the slit in directions perpendicular to each other.

34. Method according to claim 21, characterized in that each first, second and third image acquisition surface of the said at least one sensor is an array of pixels or a sub array of pixels.

35. Method according to claim 21, characterized in that the first and second image acquisition surfaces form part of a first and a second sensor respectively.

36. Method according to claim 35, characterized in that the positioning of a sensor opposite the generator is carried out by displacement of said sensor.

37. Method according to claim 21, characterized in that the first, second and third image acquisition surfaces form part of a single sensor.

* * * * *